United States Patent
Horiuchi et al.

(10) Patent No.: US 9,345,837 B2
(45) Date of Patent: *May 24, 2016

(54) GASKET FOR SYRINGE AND SYRINGE HAVING GASKET

(71) Applicant: Terumo Kabushiki Kaisha, Shibuya-ku (JP)

(72) Inventors: Aiko Horiuchi, Ashigarakami-gun (JP); Eiji Watanabe, Ashigarakami-gun (JP); Shigeru Suzuki, Ashigarakami-gun (JP); Masami Shimoda, Ashigarakami-gun (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/600,552

(22) Filed: Jan. 20, 2015

(65) Prior Publication Data

US 2015/0133873 A1 May 14, 2015

Related U.S. Application Data

(63) Continuation of application No. 12/824,773, filed on Jun. 28, 2010, now Pat. No. 8,968,260, which is a continuation of application No. PCT/JP2008/073767, filed on Dec. 26, 2008.

(30) Foreign Application Priority Data

Dec. 28, 2007 (JP) ................. 2007-339649

(51) Int. Cl.
*A61M 5/315* (2006.01)
*A61M 5/31* (2006.01)

(52) U.S. Cl.
CPC ... *A61M 5/31513* (2013.01); *A61M 2005/3104* (2013.01); *A61M 2005/3118* (2013.01); *A61M 2005/3131* (2013.01); *A61M 2205/0222* (2013.01); *A61M 2205/0238* (2013.01)

(58) Field of Classification Search
CPC ................ A61M 5/31513; A61M 2205/0222; A61M 2205/0238
See application file for complete search history.

(56) References Cited

U.S. PATENT DOCUMENTS 3,418,162 A * 12/1968 Adachi ................. C08L 83/04
427/387
4,767,414 A    8/1988 Williams et al.
(Continued)

FOREIGN PATENT DOCUMENTS

EP         1870117 A2   12/2007
JP       62-032970 A     2/1987
(Continued)

OTHER PUBLICATIONS

International Search Report (PCT/ISA/210) issued on Mar. 3, 2009, by the Japanese Patent Office as the International Searching Authority for International Application No. PCT/JP2008/073767.
(Continued)

*Primary Examiner* — Kevin C Sirmons
*Assistant Examiner* — Shefali Patel
(74) *Attorney, Agent, or Firm* — Buchanan, Ingersoll & Rooney PC

(57) ABSTRACT

A gasket for use in a syringe so formed as to liquid-tightly and slidably contact an inner surface of an outer cylinder of the syringe, the gasket including a gasket body made of an elastic body and a coating layer formed on a portion thereof which contacts at least the syringe, wherein the coating layer includes a composition containing a silicone resin which includes a condensate of a reactive silicone resin having a terminal silanol group and which has a siloxane bond derived from the silanol group, and does not contain solid fine particles.

14 Claims, 4 Drawing Sheets

(56) References Cited

U.S. PATENT DOCUMENTS

| | | | |
|---|---|---|---|
| 5,114,794 | A | 5/1992 | Sudo et al. |
| 5,207,293 | A | 5/1993 | Eden et al. |
| 5,536,582 | A | 7/1996 | Prasad et al. |
| 5,607,400 | A | 3/1997 | Thibault et al. |
| 5,807,605 | A | 9/1998 | Tingey et al. |
| 6,200,627 | B1 | 3/2001 | Lubrecht |
| 6,243,938 | B1 * | 6/2001 | Lubrecht ............ A61L 31/10 264/134 |
| 7,111,848 | B2 | 9/2006 | Tachikawa et al. |
| 7,141,042 | B2 | 11/2006 | Lubrecht |
| 2001/0021832 | A1 | 9/2001 | Numao et al. |
| 2007/0228669 | A1 | 10/2007 | Liu et al. |
| 2007/0299402 | A1 | 12/2007 | Ishii et al. |

FOREIGN PATENT DOCUMENTS

| | | |
|---|---|---|
| JP | 11-236530 A | 8/1999 |
| JP | 2001-190654 A | 7/2001 |
| JP | 2002-089717 A | 3/2002 |
| JP | 2002-506694 A | 3/2002 |
| JP | 2004-321614 A | 11/2004 |
| JP | 2005-306902 A | 11/2005 |
| JP | 2006-167110 A | 6/2006 |
| JP | 2007-244606 A | 9/2007 |
| WO | WO 99/47192 A1 | 9/1999 |

OTHER PUBLICATIONS

Written Opinion (PCT/ISA/237) issued on Mar. 3, 2009, by the Japanese Patent Office as the International Searching Authority for International Application No. PCT/JP2008/073767, and English language translation of Written Opinion.

Chinese Office Action issued Mar. 1, 2012 by the Chinese Patent Office in corresponding Chinese Application No. 200880123164.6, and partial English translation.

* cited by examiner

GASKET FOR SYRINGE AND SYRINGE HAVING GASKET

CROSS-REFERENCE TO RELATED APPLICATIONS

This application is a continuation of U.S. patent application Ser. No. 12/824,773 filed Jun. 28, 2010, which is a continuation of International Application No. PCT/JP2008/073767 filed on Dec. 26, 2008, which in turn claims priority to Japanese Application No. 2007-339649 filed on Dec. 28, 2007, the entire contents of which are incorporated herein by reference.

TECHNOLOGICAL FIELD

The present invention relates to a gasket for use in a syringe having a relatively stable sliding performance and a syringe having the gasket.

BACKGROUND

A prefilled syringe in which a liquid medicine is filled in advance has been conventionally used to prevent use of a mix-up of medicine, prevent hospital infection, disposability, and increase efficiency in hospital service. A syringe including a syringe to be used as the prefilled syringe can be constructed of an outer cylinder, a gasket slidable inside the syringe, and a plunger for operating the movement of the gasket. To enhance the sliding performance of the gasket and obtain a high degree of flow accuracy without generating a large irregularity in the discharge of the liquid medicine, silicone oil or the like is applied to a sliding portion of the outer surface of the gasket or the inner surface of the syringe as a lubricant. Depending on the kind of a liquid medicine that is used, an interaction can occur between the liquid medicine and the lubricant such as the silicone oil. When the liquid medicine is stored for a long time after the liquid medicine is filled in the syringe, the liquid medicine can be denatured by the interaction. Thus, it is difficult to use some kinds of medicines with a prefilled syringe.

The prefilled syringe to be stored for a long time with the liquid medicine filled therein can be beneficial for keeping the liquid medicine stable and eliminate the need for the lubricant.

To solve the above-described problem, as disclosed in a patent document 1 (Japanese Patent Publication Laid-Open No. 62-32970) and a patent document 2 (Japanese Patent Publication Laid-Open No. 2002-089717, U.S. Pat. No. 7,111,848), prefilled syringes were proposed in which the surface of the gasket is covered with the fluorine resin which is a material having a lower friction coefficient than the material of the gasket body to eliminate the use of the lubricant.

The present applicant proposed the gasket having the coating layer composed of the fluorine resin, the silicon resin, and the urethane resin, as disclosed in a patent document 3 (Japanese Patent Publication Laid-Open No. 2004-321614); and the gasket having the coating layer composed of the film made of the composition containing the sliding property-imparting component and the flexibility-imparting component and of the fine particles held by the film to form the rough surface on the gasket, as disclosed in a patent document 4 (Japanese Patent Publication Laid-Open No. 2006-167110).

Patent document 1: Japanese Patent Publication Laid-Open No. 62-32970

Patent document 2: Japanese Patent Publication Laid-Open No. 2002-089717, U.S. Pat. No. 7,111,848

Patent document 3: Japanese Patent Publication Laid-Open No. 2004-321614

Patent document 4: Japanese Patent Publication Laid-Open No. 2006-167110

The gaskets disclosed in the patent document 1 (Japanese Patent Publication Laid-Open No. 62-32970) and the patent document 2 (Japanese Patent Publication Laid-Open No. 2002-089717, U.S. Pat. No. 7,111,848) are expected to be effective in dependence on a use condition. But in a preparation for a prefilled syringe demanded to discharge the liquid medicine under a high pressure and have the performance of stably discharging the liquid medicine little by little with a very high accuracy for a long time by using a syringe pump or the like, liquid-tightness and sliding performance which are fundamental performance demanded for the syringe are still in a trade-off relationship. A syringe which allows these performances to be compatible with each other at a high level and has a higher performance is needed.

That is, in administration of the liquid medicine by using the syringe pump, when the liquid medicine is discharged in a condition where the flow rate is so low that the flow of the liquid medicine is invisible (for example, in the syringe having a diameter of about 24 mm, a moving speed of a gasket when it is made to discharge in 1 mL/hour is about 2 mm/hour), an unstable discharge state called pulsation is liable to occur. Thus there is a fear that accurate administration of the liquid medicine is prevented.

The gaskets disclosed in the patent document 3 (Japanese Patent Publication Laid-Open No. 2004-321614) and the patent document 4 (Japanese Patent Publication Laid-Open No. 2006-167110) are liquid-tight and have stable sliding performance without applying a lubricant to the sliding surface thereof. But in the former, materials forming the coating layer are used in a wide variety and hence the former has problems in terms of production and cost. The latter has a problem that fine particles held by the coating layer cause the formation of the coating layer to be difficult.

SUMMARY

Exemplary aspects of a gasket and syringe have been developed to provide an improved gasket and syringe. For example, according to exemplary aspects, a gasket having relatively stable sliding performance without applying a lubricant to a sliding surface thereof and a syringe having the gasket, are provided.

Exemplary aspects are as follows:

A gasket for use in a syringe so formed as to liquid-tightly and slidably contact an inner surface of an outer cylinder of the syringe. The gasket comprises a gasket body made of an elastic body and a coating layer formed on a portion thereof which contacts at least the syringe. The coating layer comprises a composition containing silicone resin which comprises a condensate of reactive silicone having a terminal silanol group, and wherein the condensate contains a siloxane bond derived from the silanol group. The coating layer does not contain solid fine particles.

Also provided is a syringe that has an outer cylinder, the above-described gasket slidably accommodated inside the outer cylinder, and a plunger which has been mounted on the gasket or can be mounted thereon.

DETAILED DESCRIPTION

A gasket of an exemplary embodiment is described below. The gasket 1 slidably contacts an inner surface of an outer cylinder (barrel) of a syringe and has a coating layer 3 formed on a portion thereof which contacts the syringe. The coating layer 3 is composed of a composition containing a specific silicone resin which is described later.

A gasket of an exemplary embodiment is described below, in which the gasket is used for and applied to the syringe.

The gasket 1 of this embodiment can be used for a syringe and liquid-tightly and slidably accommodated inside an outer cylinder 11. The gasket 1 has the coating layer 3 disposed on a portion thereof which contacts the outer cylinder 11. The coating layer 3 contains the specific silicone resin to be described later. The gasket 1 has a core part 2 and the coating layer 3 formed on a portion, of at least an outer surface of the core part 2, which contacts the inner surface of the outer cylinder 11. The coating layer 3 may be formed on the entire outer surface of the core part 2.

Figure 1:
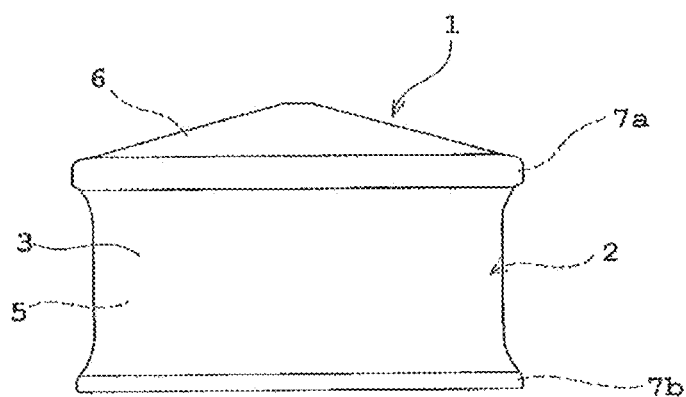
FIG. 1 is a front view showing a gasket of an exemplary embodiment.
Figure 2:
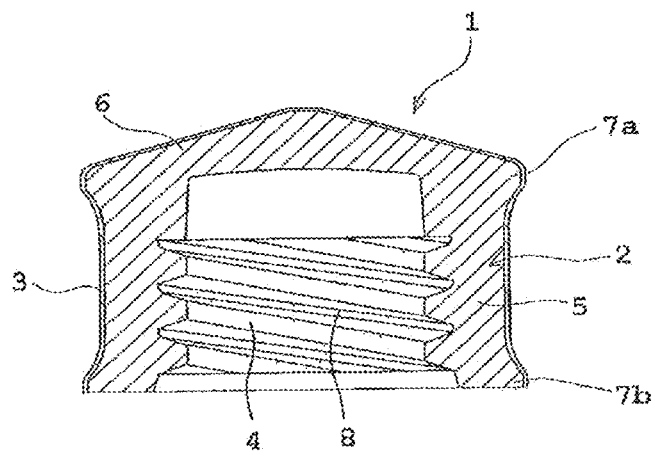
FIG. 2 is a sectional view of the gasket shown in FIG. 1, according to an exemplary embodiment.
Figure 3:
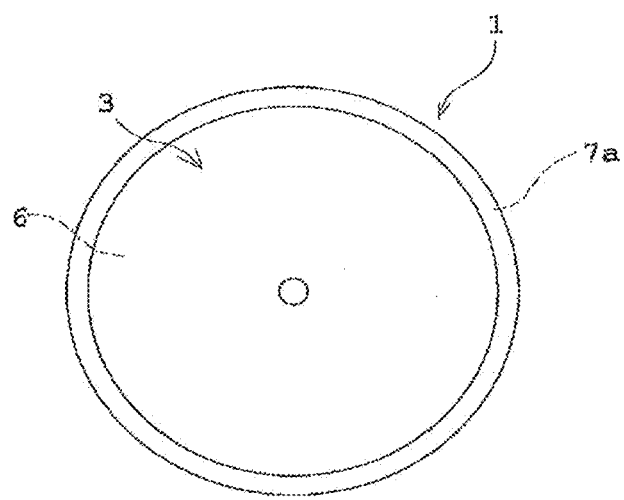
FIG. 3 is a plan view of the gasket shown in FIG. 1, according to an exemplary embodiment.
Figure 4:
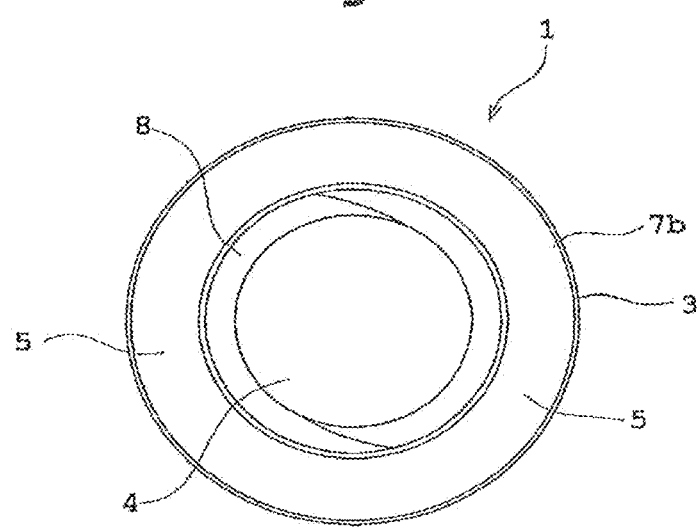
FIG. 4 is a bottom view of the gasket shown in FIG. 1, according to an exemplary embodiment.
Figure 5:
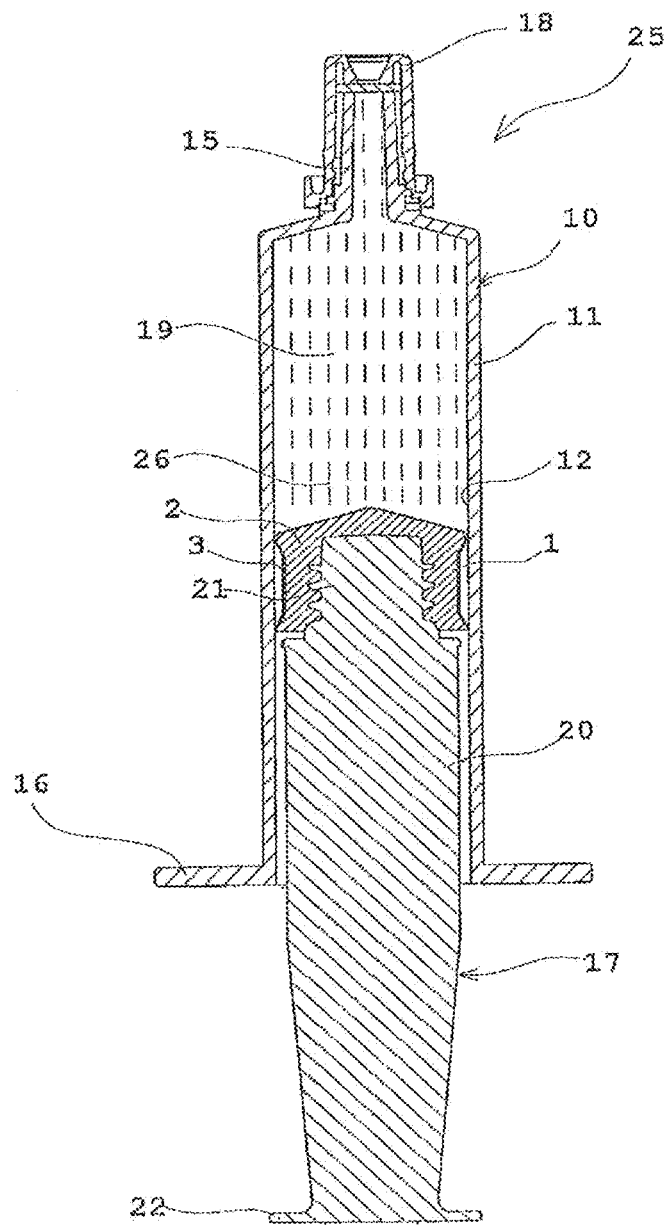
FIG. 5 is a sectional view of a prefilled syringe in which the gasket shown in FIG. 1 is used, according to an exemplary embodiment.

As shown in FIGS. 1, 2, and 5, the core part 2 of the gasket 1 for use in the syringe has a main body 5 extending in an almost equal diameter; a tapered portion 6, disposed at a distal side of the main body 5, whose diameter decreases taperingly to the distal end thereof; a plunger-mounting portion 4 provided inside the main body 5 from a proximal end thereof toward a distal side thereof; a distal-side annular rib 7a provided on a side surface of the distal portion of the main body 5; and a proximal-side annular rib 7b provided on a side surface of the proximal portion of the main body 5. As shown in FIGS. 2 and 4, the plunger-mounting portion 4 is formed as an approximately columnar concave portion which is disposed inside the main body 5 and extends from the proximal end of the main body 5 to a position in the vicinity of the distal end thereof. A screwing portion 8 capable of engaging a screwing portion formed at a distal end of a plunger is formed on a side surface of the concave portion. A distal-end surface of the concave portion is formed almost flatly. The plunger-mounting portion 4 does not necessarily have to be formed as the screwing portion, but may be formed as an engaging portion which engages the distal portion of the plunger.

The outer diameters of the annular ribs 7a and 7b are formed a little larger than the inner diameter of the outer cylinder 11 for use in the syringe. Therefore the annular ribs 7a and 7b compressively deform inside the outer cylinder 11. In the embodiment, two annular ribs are formed, but one or three or more annular ribs may be formed.

As a material composing the core part 2, an elastic material can be used. The elastic material is not limited to a specific one, but rubber materials (specifically, vulcanized rubber materials) such as natural rubber, isoprene rubber, butyl rubber, chloroprene rubber, nitrile-butadiene rubber, styrene-butadiene rubber, and silicone rubber; styrene elastomer and hydrogenated styrene elastomer; and mixtures of the styrene elastomer and polyolefins such as polyethylene, polypropylene, polybutene, and α-olefin copolymers; mixtures of the styrene elastomer and oil such as liquid paraffin, process oil; and mixtures of the styrene elastomer and powdery inorganic substances such as talc, cast, mica, and the like are listed. Further it is possible to use a polyvinyl chloride elastomer, an olefin elastomer, a polyester elastomer, a polyamide elastomer, a polyurethane elastomer, and mixtures of these elastomers as materials composing the core part 2. As the composing material, the diene rubbers and the styrene elastomer are preferable because these rubbers and elastomers have elastic properties and can be sterilized by γ (gamma) ray, electron beams, and high-pressure steam.

In an exemplary embodiment, the coating layer 3 is formed at least at the portion where the annular ribs are disposed. More specifically, the coating layer 3 can be formed at the distal-side annular rib 7a and the proximal-side annular rib 7b. The thickness of the coating layer 3 can be 1 to 30 μm, for example, 3 to 10 μm. When the thickness of the coating layer 3 is not less than 1 μm, the coating layer 3 can display good slidable performance. When the thickness of the coating layer 3 is not more than 30 μm, the coating layer 3 does not adversely affect the elasticity of the gasket. In an exemplary embodiment, the coating layer 3 does not contain fine particles. Solvent-based silicone resin dissolved in an organic solvent and water-based silicone resin emulsified and dispersed in water can be used. But from the viewpoint of the influence on the material of the gasket or the aptitude as a liquid medicine accommodation container, the water-based silicone resin can be used. The coating layer 3 can be constructed of a resin composed of a material having a low friction coefficient rather than the elastic material composing the gasket body 1.

The coating layer 3 can be composed of a composition containing a reactive silicone resin having a terminal silanol group and does not contain solid fine particles.

In an exemplary embodiment, the coating layer 3 can be composed of a composition containing silicone resin which contains or consists of a condensate of the reactive silicone resin having the terminal silanol group, wherein the condensate has a siloxane bond derived from a silanol group. In an exemplary embodiment, the coating layer 3 does not contain solid fine particles.

The composition containing the reactive silicone resin can be a thermosetting silicone resin or room temperature-curing silicone resin. For example, it can be beneficial that the composition containing the reactive silicone resin is the thermosetting silicone resin from the standpoint of workability and the like.

As the reactive silicone, polydimethylsiloxane having the terminal silanol group can be used. The reactive silicone can have the silanol group at both terminals thereof. When polysiloxane silicone having the terminal silanol group is used as the reactive silicone, the condensate of the reactive silicone has siloxane bonds in its entire main chain.

As the reactive silicone having the terminal silanol group, the polysiloxane silicone having the silanol group at both terminals thereof can be used. Both-terminal polydimethylsiloxane silanol, both-terminal polydiphenylsiloxane silanol, both-terminal diphenylsiloxane silanol-dimethylsiloxane copolymer can be used. The form of the reactive silicone is not limited to a specific one, but it is possible to use the above-described reactive silicone siloxane compounds, polysiloxane, consisting of the condensate of the reactive silicone siloxane compound, which is dispersed, emulsified, and dissolved in an aqueous medium, copolymer emulsion formed by copolymerizing an alkoxysilyl group-containing vinyl monomer with other vinyl monomer, and emulsion formed by compositing the polysiloxane with an organic polymer.

The resin composition forming the coating layer 3 can contain a second silicone compound different from the reactive silicone resin having the silanol group or the siloxane bond. As the second silicone compound, alkylalkoxysilane, phenylalkoxysilane, alkylphenoxysilane, aminoalkylalkoxysilane, and glycidoxyalkylalkoxysilane can be used.

The composition forming the coating layer 3 can contain the alkylalkoxysilane or the phenylalkoxysilane as the second silicone compound and the aminoalkylalkoxysilane and/or the glycidoxyalkylalkoxysilane as a third silicone compound.

The resin composition forming the coating layer 3 can contain the alkylalkoxysilane or the phenylalkoxysilane as the second silicone compound, the aminoalkylalkoxysilane as the third silicone compound, and the glycidoxyalkylalkoxysilane as a fourth silicone compound.

As the second silicone compound, the alkylalkoxysilane, the alkylphenoxysilane, and the phenylalkoxysilane can be used. The alkylalkoxysilane has at least one alkyl group having 1 to 20 carbon atoms and at least one alkoxy group having 1 to 4 carbon atoms. As the alkylalkoxysilane, methyltrimethoxysilane, methyltriethoxysilane, methyltriisobutoxysilane, methyltributoxysilane, methylsec-trioctyloxysilane, isobutyltrimethoxysilane, cyclohexylmethyldimethoxysilane, diisopropyldimethoxysilane, propyltrimethoxysilane, diisobutyldimethoxysilane, n-octylmethoxysiloxane, ethyltrimethoxysilane, dimethyldimethoxysilane, octyltriethoxysilane, hexyltrimethoxysilane, hexyltriethoxysilane, octamethylcyclotetrasiloxane, methyltri(acryloyloxyethoxy)silane, lauryltriethoxysilane, stearyltrimethoxysilane, stearyltriethoxysilane, ethyltriethoxysilane, propyltriethoxysilane, butyltriethoxysilane, butyltrimethoxysilane, pentyltrimethoxysilane, pentyltriethoxysilane, heptyltrimethoxysilane, heptyltriethoxysilane, octyltrimethoxysilane, nonyltrimethoxysilane, nonyltriethoxysilane, decyltrimethoxysilane, decyltriethoxysilane, undecyltrimethoxysilane, undecyltriethoxysilane, dodecyltrimethoxysilane, dodecyltriethoxysilane, tridecyltrimethoxysilane, tridecyltriethoxysilane, tetradecyltrimethoxysilane, tetradecyltriethoxysilane, pentadecyltrimethoxysilane, pentadecyltriethoxysilane, hexadecyltrimethoxysilane, hexadecyltriethoxysilane, heptadecyltrimethoxysilane, heptadecyltriethoxysilane, octadecyltrimethoxysilane, octadecyltriethoxysilane, nonadecyltrimethoxysilane, nonadecyltriethoxysilane, eykosiltrimethoxysilane, eykosiltriethoxysilane, can be used.

As the alkylphenoxysilne, methyltriphenoxysilane can be used. As the phenoxyalkoxysilane, phenyltrimethoxysilane, phenyltriethoxysilane, diphenyldimethoxysilane, diphenyldiethoxysilane, can be used.

As the second silicone compound, it is also possible to use methyltri(glycidyloxy)silane, tri methylchlorosilane, di methylchlorosilane, methyltrichlorosilane, tetraethoxysilane, heptadecafluorodecyltrimethoxysilane, tridecafluorooctyltrimethoxysilane, tetrapropoxysilane.

As the second silicone compound, the aminoalkylalkoxysilane can be used. As the aminoalkylalkoxysilane, 3-aminopropyltriethoxysilane, 3-(2-aminoethyl)aminopropyltrimethoxysilane, 3-(2-aminoethyl)aminopropylmethyldimethoxysilane, 3-aminopropyltrimethoxysilane, 3-phenylaminopropyltrimethoxysilane, can be used.

As the second silicone compound, the glycidoxyalkylalkoxysilane can be used. As the glycidoxyalkylalkoxysilane, 3-glycidoxypropyltrimethoxysilane, 3-glycidoxypropyltriethoxysilane, 3-glycidoxypropylmethyldiethoxysilane, 3-glycidoxypropylmethyldimetoxysilane, 2-(3,4-epoxycyclohexyl)ethyltrimethoxysilane, can be used.

As the second silicone compound, it is possible to use silane compounds such as 3-ureidopropyltriethoxysilane, diaryldimethylsilane, n-octyldimethylchlorosilane, tetraethoxysilane, trifluoropropyltrimethoxysilane.

The composition forming the coating layer 3 can contain the second and third silicone compounds. The second silicone compound can be selected from among the alkylalkoxysilane, the alkylphenoxysilane, and the phenylalkoxysilane. As the third silicone compound, the aminoalkylalkoxysilane or the glycidoxyalkylalkoxysilane can be used. The composition forming the coating layer 3 can contain the second, third, and fourth silicone compounds. The second silicone compound can be selected from among the alkylalkoxysilane, the alkylphenoxysilane, and the phenylalkoxysilane. As the third silicone compound, the aminoalkylalkoxysilane can be used. As the fourth silicone compound, glycidoxyalkylalkoxysilane can be used.

In an exemplary embodiment, the coating layer 3 formed on the gasket does not contain the "solid fine particle". The "solid fine particle" herein means a particle having a size to such an extent as to affect the roughness of the outer surface of the coating layer 3 when the coating layer 3 is formed. Specifically the "solid fine particle" means a particle having a diameter larger than 10% of the thickness of the coating layer 3.

Because the gasket 1 has the above-described coating layer 3, the gasket 1 can have a stable sliding performance without applying a lubricant to the sliding surface thereof and can be capable of maintaining sealing performance inside the medicine accommodation space. The initial sliding resistance value of the coating layer (in other words, gasket having coating layer) can be not more than a maximum value of the dynamic sliding resistance value thereof. The gasket satisfying the above-described condition can be capable of starting favorable initial sliding and does not make an excessive initial movement.

As the aqueous silicone resin, it is possible to use polysiloxane complex aqueous emulsion composed of a crosslinked polymer forming the core part, a non-crosslinked polymer forming a shell portion covering the core part, and polysiloxane disposed in the vicinity of the surface of the shell.

An exemplary method of forming the coating layer 3 is described below. In the method of forming the coating layer, a coating solution containing components composing the silicone resin can be mixed with one another in amounts. The resulting material can be dispersed and suspended in purified water. The coating layer can be obtained by applying the coating solution to the clean surface of the gasket and thereafter curing it. At this time, the coating solution can be applied to the surface of the gasket by carrying out a known method such as a dip coating method, a spraying method, and the like. It can be preferable to spray the coating solution to the surface of the object to be coated with the object being rotated (specifically, at 100 to 600 rpm). In applying the coating solution to the surface of the gasket by spraying it, it can be preferable to do so after heating the portion of the gasket to be coated to 60 to 120 degrees C. The coating solution can be rapidly fixed to the surface of the portion of the gasket to be coated without water repellence.

As the method of curing the coating solution, it can be left at a normal temperature, but it can be preferable to harden it by heating it.

The method of thermally curing the coating solution is not limited to a specific method, provided that the base material of the gasket is not modified or deformed. It is possible to use conventional methods such as hot air drying and a drying oven using infrared rays or a method of using a drier to be operated under a reduced pressure. The thickness of the coating layer to be formed can be 1 to 30 μm, for example, 3 to 10 μm. Such a coating layer can be easily formed by appropriately controlling the concentration of the mixed solution, the dipping method, and the spraying method.

In preparing the coating solution containing the silicone resin, a catalyst for accelerating thermosetting can be used as an additive.

As the catalyst, acid, alkali, amine, organic salts of metals, titanate, and borate can be used. Organic acid salts such as zinc octylate, iron octylate or organic acid salts of cobalt, tin, and lead can be used.

As the organic acid salts of tin, it is possible to use bis(2-ethylhexanoate)tin, bis(neodecanoate)tin, di-n-butylbis(2-ethylhexylmalate)tin, di-n-butylbis(2,4-pentanedionate)tin, di-n-(butylbutoxychloro)tin, di-n-(butyldiacetoxy)tin, tin di-n-butyldilaurate, tin dimethyldineodecanoate, tin dimethylhidroxy(oleate), and tin dioctyldilaurate.

In preparing the coating solution containing the silicone resin, additives such as a surface active agent, alcohol, and the like can be used to uniformly emulsify, suspend, and disperse the coating solution.

As the surface active agent, anion surface active agents can be used. Any of the anion surface active agents can be used. It is possible to use aliphatic monocarboxylate, polyoxyethylene alkyl ether carboxylate, N-acylsarcosinate, N-acyl glutamate, dialkyl sulfosuccinate, alkanesulfonate, alpha olefin sulfonate, straight chain alkylbenzenesulfonate, molecular chain alkylbenzenesulfonate, naphthalene sulfonate-formaldehyde condensate, alkylnaphthalene sulfonate, N-methyl-N-acyltaurine, alkyl sulfate, polyoxyethylenealkyl ether sulfate, fat sulfate salt, alkyl phosphate, polyoxyethylenealkyl ether sulfate and polyoxyethylenealkylphenyl ether sulfate.

Nonionic surface active agents can be used. Any of the nonionic surface active agents can be used. It is possible to use polyoxyethylene alkyl ether, polyoxyalkylene derivatives, polyoxyethylene alkyl phenyl ether, polyoxyethylene sorbitan fatty acid ester, fatty acid alkanolamide, glycerin fatty acid ester, sorbitan fatty acid ester, polyoxyethylene alkylamine, and alkylalkanolamide.

The syringe 10 can have the outer cylinder 11, the gasket 1 slidably accommodated inside the outer cylinder 11, and a plunger 17 which has been mounted or can be mounted on the gasket 1.

For example, as shown in FIG. 5, the syringe 10 is constructed of the outer cylinder 11, for use in the syringe, which has a needle-mounting portion 15 disposed at the distal side thereof and a flanges 16 disposed to be opposite at the proximal end thereof; the gasket 1, for use in the syringe, which is capable of liquid-tightly and airtightly sliding on an inner surface 12 of the outer cylinder 11; the plunger 17 which has been or can be mounted on the gasket 1 for use in the syringe; a sealing member 18 for sealing the needle-mounting portion 15 of the outer cylinder 11 for use in the syringe; and a medicine-accommodating portion 19, for accommodating a medicine 26, which is formed among the sealing member 18, the inner surface 12 of the outer cylinder 11, and the gasket 1 for use in the syringe. Instead of the sealing member 18, a needle may be mounted on the needle-mounting portion 15. As shown in FIG. 5, the sealing member 18 may be of a type having a piercing portion into which a double ended needle can be directly inserted or may be of a type in which a medicine cannot be discharged until the sealing member is removed. The gasket 1 has the coating layer 3. In the syringe 10, it can be preferable that the dynamic sliding resistance value of the gasket 1 when the gasket 1 slides at a low speed (100 mm/minute) inside the outer cylinder 11 is not more than 20N. Such a low dynamic sliding resistance value can be obtained when the gasket 1 has the coating layer 3. For example, the dynamic sliding resistance value of the gasket 1 when the gasket 1 slides at the low speed (100 mm/minute) inside the outer cylinder 11 can be 1N to 20N.

According to an exemplary aspect, this medical appliance is a prefilled syringe 25 composed of the syringe 10 and the medicine 26, as shown in FIG. 5.

The outer cylinder 11 for use in the syringe has the needle-mounting portion 15 disposed at the distal portion thereof and the flange 16 disposed at the proximal end thereof. The outer cylinder 11 is made of a material transparent or semitransparent. The outer cylinder 11 can be made of a material having a low oxygen permeability or vapor permeability. The material forming the outer cylinder 11 can have a glass transition point or a melting point not less than 110 degrees C.

As the material forming the outer cylinder 11, various general-purpose rigid plastic materials can be used. Polyolefin such as polypropylene, polyethylene, poly(4-methylpentene-1), and cyclic polyolefin; polyesters such as polyethylene terephthalate, polyethylene naphthalate, and non-crystalline polyarylate; polystyrene; polyamide; polycarbonate, polyvinyl chloride; acrylic resin; acrylonitrile-butadiene-styrene copolymer, and non-crystalline polyetherimide can be used. The polypropylene, the poly(4-methylpentene-1), the cyclic polyolefin, the polyethylene naphthalate, and the non-crystalline polyetherimide can be used because these resins are transparent and resistant to heat sterilization. These resins can be used as materials to form not only a syringe barrel, but also a container capable of accommodating a medicine. It is also possible to use glass as a material to form the outer cylinder.

As shown in FIG. 5, the plunger 17 has a sectionally cross-shaped main body 20 extended axially; a plunger-side screwing portion 21, provided at the distal portion thereof, which engages the plunger-mounting portion 4; a disk-shaped gasket-pressing portion provided between the plunger-side screwing portion 21 and the main body 20; a disk portion 22, for pressing use, which is disposed at the proximal end of the main body 20; and a disk-shaped rib formed midway on the main body 20.

The medicine 26 can be contained inside the syringe 10 of this exemplary embodiment. As the medicine 26, it is possible to use a solution and a solid agent such as a powdery medicine and a freeze-dried medicine. When a liquid medicine having poor water solubility and a high adsorbability or a liquid medicine containing a surface active agent and having a low viscosity and a high degree of penetration is accommodated inside the syringe 10, silicone oil is unnecessary. When the coating layer 3 is provided at a portion which contacts an accommodated medicine, the adsorption of the medicine can be prevented. Thus it is possible to use the syringe 10 for the liquid medicine having the above-described properties.

As the material composing the plunger 17 and the sealing member 18, hard resin or semi-hard resin can be used such as, for example, polyvinyl chloride, high-density polyethylene, polypropylene, polystyrene, polyethylene terephthalate, polycarbonate, acrylic resin, and the like.

EXAMPLES

Examples are described below.

Example 1

By using butyl rubber, the core part of a gasket for use in a syringe, having a configuration shown in FIGS. 1 and 2 was produced. The core part was formed by press-molding a vulcanizable rubber composition composed of butyl rubber and an additive added thereto. Describing the configuration of the obtained core part, it had a length of 20 mm, an outer diameter of 23.7 mm at distal-side and proximal-side annular ribs, a length of 10 mm between the center of the distal-side annular rib and the center of the proximal-side annular rib, an outer diameter of 21.5 mm at an identical diameter portion between the distal-side annular rib and the proximal-side annular rib, a length (depth) of 8 mm in the plunger-mounting concave portion having a female screw at an inner side thereof, an inner diameter of 14.5 mm at the distal side of the plunger-mounting concave portion, and an inner diameter of 15 mm at the rear side of the plunger-mounting concave portion.

Thereafter 29 parts by weight of silicone resin and one part by weight of tin dioctyldilaurate were added to 66 parts by weight of purified water to prepare a coating solution. As the silicone resin, substances shown below were mixed with one another by using straight-chain sodium alkylbenzene sulfonate.

1) 25 parts by weight of 1501 Fluid (commercial name, produced by Dow Corning Toray Co., Ltd.) containing both-terminal polydimethyl siloxane silanol as its main component.

2) 0.1 parts by weight of Z-6366 (commercial name, produced by Dow Corning Toray Co., Ltd.) containing methyltrimethoxysilane as its main component.

3) One part by weight (resin ratio: 50%) of a mixture of Z-6011 (commercial name, produced by Dow Corning Toray Co., Ltd.) containing 3-aminopropyltriethoxysilane as its main component and an ethanol solution of maleic anhydride.

4) 0.5 parts by weight of Z-6040 (commercial name, produced by Dow Corning Toray Co., Ltd.) containing 3-glycidoxypropyltrimethoxysilane as its main component.

After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 8 μm. This gasket was set as the example 1.

Example 2

29 parts by weight of the silicone resin as in the case of the example 1 and one part by weight of the tin dioctyldilaurate were added to 66 parts by weight of the purified water to prepare a main agent.

Five parts by weight of purified water was added to 8 parts by weight of the main agent and both were mixed with each other to prepare a coating solution. After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 5 μm. This gasket was set as the example 2.

Example 3

29 parts by weight of the silicone resin and one part by weight of the tin dioctyldilaurate were added to 66 parts by weight of the purified water to prepare a coating solution. As the silicone resin, substances shown below were mixed with one another by using the straight-chain sodium alkylbenzene sulfonate.

1) 25 parts by weight of DMS-S14 (commercial name, produced by GELEST Inc.) containing the both-terminal polydimethyl siloxane silanol as its main component.

2) 0.1 parts by weight of SIP6560.0 (commercial name, produced by GELEST Inc.) containing the methyltrimethoxysilane as its main component.

3) One part by weight (resin ratio: 50%) of a mixture of SIA0610.0 (commercial name, produced by GELEST Inc.) containing the 3-aminopropyltriethoxysilane as its main component and the ethanol solution of the maleic anhydride.

4) 0.5 parts by weight of SIG5840.1 (commercial name, produced by GELEST Inc.) containing the 3-glycidoxypropyltrimethoxysilane as its main component.

After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 8 μm. This gasket was the as the example 3.

Example 4

29 parts by weight of the silicone resin and one part by weight of the tin dioctyldilaurate were added to 66 parts by weight of the purified water to prepare a coating solution. As the silicone resin, substances shown below were mixed with one another by using the straight-chain sodium alkylbenzene sulfonate.

1) 25 parts by weight of YR3204 (commercial name, produced by Momentive Performance Materials Japan, Limited Liability Company) containing polyalkylphenylsiloxane having terminal silanol group as its main component.

2) 0.1 parts by weight of TSL8178 (commercial name, produced by Momentive Performance Materials Japan, Limited Liability Company) containing the phenyltriethoxysilane as its main component.

3) One part by weight (resin ratio: 50%) of a mixture of TSL8331 (commercial name, produced by Momentive Performance Materials Japan, Limited Liability Company) containing the 3-aminopropyltriethoxysilane as its main component and the ethanol solution of the maleic anhydride.

4) 0.5 parts by weight of TSL8350 (commercial name, produced by Momentive Performance Materials Japan, Limited Liability Company) containing the 3-glycidoxypropyltrimethoxysilane as its main component.

After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 8 μm. This gasket was set as the example 4.

Comparison Example 1

29 parts by weight of the silicone resin as in the case of the example 1 and one part by weight of the tin dioctyldilaurate were added to 66 parts by weight of the purified water to prepare a main agent.

In addition, 52 parts by weight of silicone rubber powder, and 2 parts by weight of the polyoxyethylenealkyl ether were added to 46 parts by weight of the purified water to prepare a fine powder liquid. As the silicone rubber powder, silicone rubber powder KMP-600 (commercial name, produced by Shin-Etsu Chemical Industry Co., Ltd.) was used. Five parts by weight of the purified water and three parts by weight of the fine powder liquid were added to five parts by weight of the main agent, and they were mixed with one another to prepare a coating solution.

After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 8 μm. This gasket was set as the comparison example 1.

Comparison Example 2

29 parts by weight of the silicone resin as in the case of the example 1 and one part by weight of the tin dioctyldilaurate were added to 66 parts by weight of the purified water to prepare a main agent.

In addition 52 parts by weight of the silicone rubber powder KMP-600 (commercial name, produced by Shin-Etsu Chemical Industry Co., Ltd.) and 2 parts by weight of the polyoxyethylenealkyl ether were added to 46 parts by weight of the purified water to prepare a fine powder liquid.

After five parts by weight of the purified water and two parts by weight of the fine powder liquid were added to six parts by weight of the main agent, they were mixed with one another to prepare a coating solution.

After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 8 μm. This gasket was set as the comparison example 2.

Comparison Example 3

29 parts by weight of the silicone resin as in the case of the example 1 and one part by weight of the tin dioctyldilaurate were added to 66 parts by weight of purified water to prepare a main agent.

In addition 52 parts by weight of the silicone rubber powder KMP-600 (commercial name, produced by Shin-Etsu Chemical Industry Co., Ltd.), and 2 parts by weight of the polyoxyethylenealkyl ether were added to 46 parts by weight of the purified water to prepare a fine powder liquid.

After five parts by weight of the purified water and one part by weight of the fine powder liquid were added to seven parts by weight of the main agent, they were mixed with one another to prepare a coating solution.

After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 8 μm. This gasket was set as the comparison example 3.

Comparison Example 4

One part by weight of fluorine resin, 10 parts by weight of the silicone resin, three parts by weight of urethane resin, 20 parts by weight of talc fine powder (average particle diameter: approximately 3 μm), one part by weight of N-methylpyrrolidone, one part by weight of butylcarbitol, and one part by weight of polyoxyethylenealkyl ether were added to 100 parts by weight of the purified water to prepare a coating solution. As the fluorine resin, Polyflon (product name, registered trademark) TFE (produced by Daikin Industries, Ltd.) containing tetrafluoroethylene as its main component was used. As the silicone resin, SE1980 (product name, produced by Dow Corning Toray Co., Ltd.) which is aqueous silicon resin (aqueous silicone compound) was used. As the urethane resin, Rozan 1100 (product name, produced by Toyo Polymer Co., Ltd.) which is aqueous urethane resin was used.

As a silane coupling agent, TSL8310 (commercial name, produced by Momentive Performance Materials Japan, Limited Liability Company) containing vinyltrimethoxysilane as its main component was prepared.

After five parts by weight of the silane coupling agent was added to 95 parts by weight of the main agent, both agents were mixed with each other to prepare a coating solution.

After at a room temperature and a normal pressure, the gasket core member produced in the above-described manner was heated to 90 degrees C. for 30 minutes, the gasket core member was rotated (300 rpm) on its axis with the coating solution having the above-described composition being sprayed to the gasket core member from the side surface of the gasket core member which was rotating. Thereafter the coating solution was dried at 150 degrees C. for 30 minutes. Thereby the gasket was formed. Thereafter to wash extra coating solution which remained on the produced gasket, cleaning was performed with purified water having a temperature not less than 80 degrees C. The average thickness of a coating layer formed on the surface of the core member was about 10 μm. This gasket was set as the comparison example 4.

Experiment 1: Stability of Coating Solution

The stability of the coating solutions prepared in the examples 1 through 4 and the comparison examples 1 through 4 were evaluated. The appearances of the coating solutions after they were refrigerated for one month are as shown in table 1.

TABLE 1

| | Appearance | |
|---|---|---|
| | Immediately after preparation | After one-month refrigeration |
| Example 1 | White emulsion | No change from appearance immediately after preparation |
| Example 2 | White emulsion | No change from appearance immediately after preparation |
| Example 3 | White emulsion | No change from appearance immediately after preparation |
| Example 4 | White emulsion | No change from appearance immediately after preparation |
| Comparison example 1 | White emulsion | White precipitation is confirmed. |
| Comparison example 2 | White emulsion | White precipitation is confirmed. |
| Comparison example 3 | White emulsion | White precipitation is confirmed. |
| Comparison example 4 | White emulsion | Grey precipitation is confirmed. |

Experiment 2: Friction Coefficient Measurement Test

After the coating solutions prepared in the example 2 and the comparison example 1 were applied to an EPDM rubber sheet, having a size of 30 mm×50 mm and a thickness of 2 mm, which was heated to 90 degrees C. for 30 minutes with a brush, the coating solutions were dried at 150 degrees C. for 30 minutes. Thereafter the rubber sheet was left still for 24 hours at a room temperature. By applying a load of 100 to 1000 g to the rubber sheet, a stress generated when the rubber sheet was horizontally moved on the glass plate at a speed of 1000 mm/minute was measured by using the method in accordance with JIS K7125 and a friction tester (reciprocating wear tester Type: 30, produced by Shinto Science Ltd.), and a dynamic friction coefficient ($\mu d$) and a static friction coefficient ($\mu s$) were found. Table 2 shows the results.

TABLE 2

| | Load 100 g | | Load 500 g | | Load 1000 g | |
|---|---|---|---|---|---|---|
| | μd | μs | μd | μs | μd | μs |
| Example 2 | 0.2 | 0.6 | 0.2 | 0.6 | 0.2 | 0.5 |
| Comparison example 1 | 0.1 | 0.3 | 0.1 | 0.3 | 0.1 | 0.2 |

Experiment 3: Sliding Resistance Measurement Test

As a material of outer cylinders for syringes, polypropylene (produced by Japan Polychem Corporation) was injection-molded to produce outer cylinders for syringes having the configuration shown in FIG. 5. The cylindrical portion of each outer cylinder for use in the syringe had an inner diameter of 23.5 mm and a length of 95 mm. The polypropylene (produced by Japan Polychem Corporation) was injection-molded to form plungers having the configuration shown in FIG. 5.

The outer cylinders for the syringes, the gaskets of the examples 1 and 2 and the comparison examples 1 through 4, and the plungers were assembled to form syringes.

The sliding resistance value of each syringe was measured by an autograph (model name: EZ-Test, manufactured by Shimadzu Corporation). More specifically, with the distal end of each syringe and the proximal end of the plunger fixed to a fixing portion of the autograph to which the object to be measured, the plungers were moved downward 60 mm at a speed of 100 mm/minute to measure the initial sliding resistance value and the maximum sliding resistance value (N). Table 3 shows the results.

As shown in table 3, the syringes using the gaskets of the examples 1 and 2 and the comparison examples 1 through 4 were almost equal in the initial sliding resistance value and maximum sliding resistance value thereof. In addition, each of the syringes had a small difference between the initial sliding resistance value and maximum sliding resistance value thereof. Thus there is little fear that a liquid medicine was discharged from the syringes in an amount more than a predetermined amount when the plunger was started to be pressed. Therefore the syringes were capable of discharging the liquid medicine safely and accurately. Favorable results that the initial sliding resistance value and the maximum sliding resistance value were not more than 10N were obtained.

In the experiment 2 in which a test system conforming to JIS K7125 was adopted, comparing a rubber sheet formed by using the coating solution (example 1) not containing the solid fine particles and a rubber sheet formed by using the coating solution (comparison example 2) containing the solid fine particles with each other, it was shown that the rubber sheet formed by using the coating solution containing the solid fine particles had a lower friction coefficient and a higher sliding performance than the rubber sheet formed by using the coating solution not containing the solid fine particles. But the results obtained from the sliding-measuring test conducted in the experiment 2 in which the gasket and the syringe were combined with each other indicate that the coating solution containing the solid fine particles is not superior to the coating solution not containing the solid fine particles, but the coating solution not containing the solid fine particles had also a favorable sliding performance.

TABLE 3

|  | Sliding resistance value (N) | Pressure test | High penetration liquid sealing performance | Surface roughness (μm) Ra | Rz |
| --- | --- | --- | --- | --- | --- |
|  | Maximum | | | | |
| Example 1 | 5.3 | 7.4 | Passed | Passed | 1.38 | 35.11 |
| Example 2 | 5.9 | 7.3 | Passed | Passed | 1.47 | 43.93 |
| Comparison example 1 | 4.2 | 8.3 | Passed | Passed | 3.09 | 102.87 |
| Comparison example 2 | 4.5 | 6.7 | Passed | Passed | 2.35 | 79.39 |
| Comparison example 3 | 5.6 | 6.9 | Passed | Passed | 2.16 | 72.67 |
| Comparison example 4 | 9.3 | 13.1 | Passed | Passed | 2.92 | 56.74 |

The above-described outer cylinders for the syringes, the gaskets of the example 1 and the comparison example 4, and the above-described plungers were assembled to form syringes. Thereafter 40 mL of purified water was injected to each syringe barrel. After a sealing member was fitted on the leading end of the syringe barrel to seal it and perform autoclave sterilization, sliding resistance values were measured by the autograph (model name: EZ-Test, manufactured by Shimadzu Corporation) in the above-described manner. The initial sliding resistance value and the maximum sliding resistance value (N) were measured at a test speed of 20 to 500 mm/minute. Table 4 shows the results.

As shown in table 4, it has been found that at a test speed lower than 100 mm/minute, the syringe using the gasket of the example 1 had a lower sliding resistance value than the syringe using the gasket of the comparison example 4 containing fine particles. Thus it has been found that the sliding performance of the former at a speed suitable for injecting a medicine into the vein is more favorable than that of the latter.

The number of samples in each test is set to 10, and numerical values in table 4 show the average of 10 samples.

TABLE 4

| | Maximum sliding resistance value (N) | | | | | |
| --- | --- | --- | --- | --- | --- | --- |
| | 20 mm/min | 30 mm/min | 50 mm/min | 100 mm/min | 200 mm/min | 500 mm/min |
| Example 1 | 9.6 | 10.1 | 11.7 | 15.7 | 21.2 | 29.5 |
| Comparison example 4 | 10.2 | 11.9 | 12.5 | 15.6 | 19.2 | 23.9 |

As a material forming an outer cylinder for a syringe, the outer cylinder for the syringe having the configuration shown in FIG. 5 was formed by using glass (produced by Shiotani Glass Co., Ltd.). The cylindrical portion of the outer cylinder for the syringe had an inner diameter of 23 mm and a length of 76 mm. As a material forming a plunger, polypropylene (produced by Japan Polychem Corporation) was injection-molded to form the plunger having the configuration shown in FIG. 5.

The outer cylinder for the syringe, the gasket of the example 1, and the plunger were assembled to form the syringe. Thereafter 20 mL of purified water was injected to the outer cylinder. As in the case of the above-described manner, the sliding resistance value was measured by the autograph (model name: EZ-Test, manufactured by Shimadzu Corporation). More specifically, with the distal end of the syringe and the proximal end of the plunger fixed to the fixing portion of the autograph to which an object to be measured, the plunger was moved downward 45 mm at speeds of 20, 50, 100, and 500 mm/minute to measure the maximum sliding resistance value (N). Table 5 shows the results.

TABLE 5

| | Maximum sliding resistance value (N) | | | |
| --- | --- | --- | --- | --- |
| | 20 mm/min | 50 mm/min | 100 mm/min | 500 mm/min |
| Example 1 | 6.0 | 7.3 | 11.4 | 14.2 |

Experiment 4: Pressure Test Specified in Standard of Sterilized Syringe

As a material of outer cylinders for syringes, polypropylene (produced by Japan Polychem Corporation) was injection-molded to produce outer cylinders for the syringes having the configuration shown in FIG. 5. The cylindrical portion of each outer cylinder for use in the syringe had an inner diameter of 23.5 mm and a length of 95 mm. As a material forming plungers, polypropylene (produced by Japan Polychem Corporation) was injection-molded to form the plungers having the configuration shown in FIG. 5.

The outer cylinders for the syringes, the gaskets of the example 1 and 2 and the comparison examples 1 through 4, and the plungers were assembled to form syringes.

A test was conducted for the above-described syringes in accordance with the pressure test specified in the standard of the sterilized plastic syringe barrel which can be immediately used as it is and disposed at one-time use (notified on Dec. 11, 1998 by Director of Pharmaceutical and Medical safety Bureau in 1079 issue of Pharmaceutical Development). Table 3 shows the results.

The number of samples in the test was five. "Passed" was marked for examples and comparison examples in which all of the five samples passed inspection.

Experiment 5: Test for Examining Sealing Performance of High Penetration Liquid

As a material of outer cylinders for syringes, polypropylene (produced by Japan Polychem Corporation) was injection-molded to produce outer cylinders for the syringes having the configuration shown in FIG. 5. The cylindrical portion of each of the outer cylinders for use in the syringes had an inner diameter of 23.5 mm and a length of 95 mm. As a material forming plungers, polypropylene (produced by Japan Polychem Corporation) was injection-molded to form the plungers having the configuration shown in FIG. 5.

The outer cylinders for the syringes, the gaskets of the example 1 and 2 and the comparison examples 1 through 4, and the plungers were assembled to form syringes.

Thereafter by using "Ageless" (registered trademark) "Checker" (produced by Mitsubishi Gas Chemical Company) for use in a test for examining the sealing performance of a heat sealing portion made of a soft plastic packing material, a sealing performance test was conducted. The syringes were left overnight to visually observe liquid leak from the sliding portion of the gasket. Table 3 shows the results.

The number of samples in the test was five. "Passed" was marked for examples and comparison examples in which all of the five samples passed inspection.

Experiment 6: Surface Roughness

The surface roughness of each of the gaskets of the example 1 and 2 and the comparison examples 1 through 4 was measured. The measuring method was carried out in accordance with JIS B0601 (1994). Table 3 shows the results.

Experiment 7: Fixation Test

Plates made of polypropylene (produced by Japan Polychem Corporation) each having a size of 50 mm×70 mm and a thickness of 2 mm were prepared. In addition, after a rubber sheet (having a size of 10 mm×50 mm, thickness of 15 mm) made of butyl rubber which was also used for the gasket core member was heated to 90 degrees C. for 30 minutes, each of the coating solutions used in the example 2 and the comparison example 1 was sprayed to the rubber sheet and dried at 150 degrees C. for 30 minutes to prepare specimens.

With each specimen sandwiched between the polypropylene plate and an iron plate, a coating surface of the specimen set at the side of the polypropylene plate, and the specimen fixed with a clip, each specimen was left overnight in a thermostatic bath whose temperature was 40 degrees C., 60 degrees C., and 80 degrees C. and for 10, 20, and 30 days in the thermostatic bath whose temperature was 60 degrees C. The degree of fixation was measured by using an autograph (model name: EZ-Test, manufactured by Shimadzu Corporation). Table 6 shows the results.

As a material of outer cylinders for syringes, polypropylene (produced by Japan Polychem Corporation) was injection-molded to produce the outer cylinders for syringes having the configuration shown in FIG. 5. The cylindrical portion of each outer cylinder for use in the syringe had an inner diameter of 23.5 mm and a length of 95 mm. As a material forming plungers, polypropylene (produced by Japan Polychem Corporation) was injection-molded to form the plungers having the configuration shown in FIG. 5.

The outer cylinders for the syringes, the gaskets of the example 2 and the comparison example 1, and the plungers were assembled to form syringes. Thereafter each syringe was left overnight in a thermostatic bath whose temperature was 40 degrees C., 60 degrees C., and 80 degrees C. and for 10, 20, and 30 days in the thermostatic bath whose temperature was 60 degrees C. To evaluate the degree of fixation of the gasket to the outer cylinder for the syringe, the initial sliding resistance value of each syringe was measured by using the autograph (model name: EZ-Test, manufactured by Shimadzu Corporation). Specifically, with the distal end of each syringe and the proximal end of the plunger fixed to the fixing portion of the autograph to which an object to be measured, the plungers were moved downward 60 mm at a speed of 100 mm/minute to measure the initial sliding resistance value (N). Table 7 shows the results.

TABLE 6

| | Fixing strength (kg/5 cm2) | | | | | |
|---|---|---|---|---|---|---|
| | 40 degrees C. | 60 degrees C. one day | 80 degrees C. | 60 degrees C. | | |
| | | | | 10 days | 20 days | 30 days |
| Example 2 | 1.3 | 1.4 | 1.5 | 2.1 | 1.5 | 1.6 |
| Comparison example 1 | 0 | 0 | 0 | 0 | 0 | 0 |

TABLE 7

| | Initial sliding resistance value (N) | | | | | |
|---|---|---|---|---|---|---|
| | Time when test started | 40 degrees C. | 60 degrees C. one day | 80 degrees C. | 60 degrees C. | | |
| | | | | | 10 days | 20 days | 30 days |
| Example 2 | 5.39 | 5.39 | 5.76 | 6.12 | 6.33 | 6.44 | 7.32 |
| Comparison example 1 | 4.97 | 5.48 | 6.14 | 7.39 | 7.54 | 6.94 | 8.93 |

Comparing a rubber sheet formed by using the coating solution (example 2) not containing the solid fine particles and a rubber sheet formed by using the coating solution (comparison example 1) containing the solid fine particles with each other, it was shown that the rubber sheet formed by using the coating solution containing the solid fine particles had a lower fixation degree than the rubber sheet formed by using the coating solution not containing the solid fine particles. But from the initial sliding resistance value obtained in the sliding-measuring test conducted by combining the gasket and the syringe with each other, the results of the fixation test (table 6) indicate that the coating solution containing the solid fine particles is not superior to the coating solution not containing the solid fine particles, but there is no difference between the fixation degree of the coating solution not containing the solid fine particles and the fixation degree of the coating solution containing the solid fine particles.

Experiment 8: Test for Examining Insoluble Fine Particles.

As a material of outer cylinders for syringes, polypropylene (produced by Japan Polychem Corporation) was injection-molded to produce the outer cylinders for the syringes having the configuration shown in FIG. 5. The cylindrical portion of each outer cylinder for use in the syringe had an inner diameter of 23.5 mm and a length of 95 mm. As a material forming plungers, Polypropylene (produced by Japan Polychem Corporation) was injection-molded to form the plungers having the configuration shown in FIG. 5. The outer cylinders for the syringes, the gaskets of the example 1 and the comparison example 1, and the plungers were assembled to form syringes. Thereafter 40 mL of purified water was injected to each syringe barrel. After a sealing member was fitted on the leading end of the syringe barrel to seal it and perform autoclave sterilization, the number of insoluble fine particles in the purified water was measured after the syringe was intensely shook for 10 minutes. Table 8 shows the results.

TABLE 8

| | Number (piece) of insoluble fine particles per syringe | | |
|---|---|---|---|
| | Not less than 5 μm | Not less than 10 μm | Not less than 25 μm |
| Example 1 | 33 | 4 | 0 |
| Comparison example 1 | 144 | 24 | 0 |

Experiment 9: Test for Examining Flow Rate Accuracy with Syringe Pump

By using a syringe pump (TE-331, produced by Terumo Corporation), the flow rate accuracy of the syringe was evaluated. As a material of outer cylinders for syringes, polypropylene (produced by Japan Polychem Corporation) was injection-molded to produce the outer cylinders for the syringes having the configuration shown in FIG. 5. The cylindrical portion of each outer cylinder for use in the syringe had an inner diameter of 23.5 mm and a length of 95 mm. As a material forming plungers, polypropylene (produced by Japan Polychem Corporation) was injection-molded to form the plungers having the configuration shown in FIG. 5.

The outer cylinders for syringes, the gaskets of the example 1 and the comparison example 1, and the plungers were assembled to form syringes.

Figure 6:
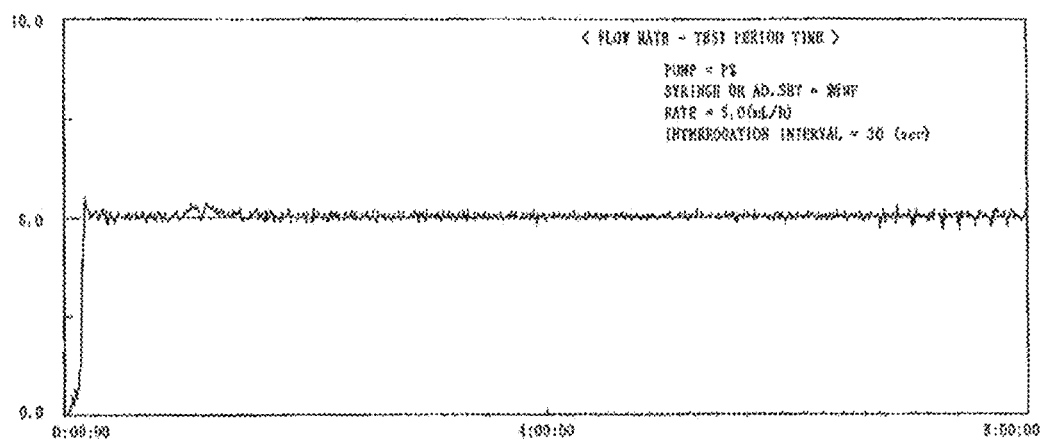
FIG. 6 shows results of the discharge characteristic of a syringe, according to an exemplary embodiment.
Figure 7:
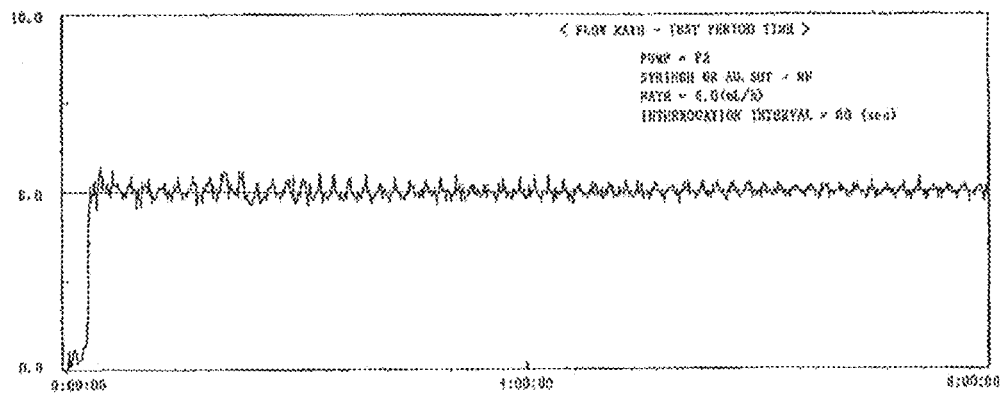
FIG. 7 shows results of the discharge characteristic of a syringe of a comparison example.

Thereafter 40 mL of purified water was injected to each syringe barrel. After a sealing member was fitted on the leading end of the syringe barrel to seal it and perform autoclave sterilization, each syringe was set on the syringe pump to discharge the purified water for eight hours at a flow rate of 5 mL/hour. By using an electronic balance, the weight of the discharged purified water was measured at intervals of 30 seconds. As a result, discharge amplitude results as shown in FIG. 6 (example 1) and FIG. 7 (comparison example 1) were obtained. As apparent from FIGS. 6 and 7, it has been confirmed that the syringe of the example 1 had smaller amplitude and more stable discharge than the comparison example 7.

The gasket disclosed by way of example here includes a number of aspects.

For example, the gasket has useful application with a syringe to liquid-tightly and slidably contact an inner surface of an outer cylinder of the syringe. The gasket has a gasket body made of an elastic body and a coating layer formed in a portion thereof which contacts at least the syringe. The coating layer is composed of a composition containing silicone resin which consists of a condensate of reactive silicone resin having a terminal silanol group and which has a siloxane bond derived from the silanol group and does not contain solid fine particles.

The gasket for use in the syringe has the coating layer disposed at the portion thereof which contacts the outer cylinder. The coating layer is composed of the composition containing the specific silicone resin. Therefore the coating layer has stable sliding performance without applying a lubricant to the sliding surface of the gasket.

The coating layer of the gasket can be formed by using the reactive silicone containing the terminal silanol group and the water-based coating agent containing the catalyst for curing the reactive silicone and can be produced stably, easily, and securely.

As compared with the coating layer containing fine particles, the coating layer of the gasket has a favorable sliding resistance value when the gasket slides at a low speed and prevents the syringe and the gasket from sticking to each other during storage. Therefore in using the syringe, it is possible to smoothly move the gasket in its initial movement and thus avoid a rapid injection and achieve injection at a constant speed.

Even in a sucking operation to be often performed to check whether a vessel has been secured, the possibility of the separation of the fine particles from the gasket is not nil in the gasket having the coating layer containing fine particles. Because the fine particles are not contained in an exemplary embodiment, the risk of the separation of the fine particles from the gasket is nil.

The embodiment of the gasket disclosed here can also be constructed with additional aspects such as described below. For example, the gasket for use in the syringe can be constructed so that the reactive silicone is polydimethylsiloxane having a terminal silanol group. The reactive silicone has the silanol group at both terminals thereof. Also, the composition contains a second silicone compound different from the silicone resin having the siloxane bond. The second silicone compound is alkylalkoxysilane, phenylalkoxysilane, aminoalkylalkoxysilane or glycidoxyalkylalkoxysilane. The composition contains alkylalkoxysilane or phenylalkoxysilane as a second silicone compound; and further contains aminoalkylalkoxysilane or/and glycidoxyalkylalkoxysilane as a third silicone compound. Additionally, the composition contains alkylalkoxysilane or phenylalkoxysilane as a second silicone compound; and further contains aminoalkylalkoxysilane as a third silicone compound; and contains glycidoxyalkylalkoxysilane as a fourth silicone compound. The silicone resin is hermosetting, and the coating layer can have a thickness of 1 to 30 µm. The initial sliding resistance value of the coating layer is not more than a maximum value of a dynamic sliding resistance value thereof, and an outer cylinder made of plastics can also be used. The syringe with which the gasket is usable comprises an outer cylinder, the gasket is slidably accommodated inside the outer cylinder; and a plunger is either mounted on the gasket or is adapted to be mounted on the gasket. The syringe can be filled with a liquid medicine. The dynamic sliding resistance value of the gasket when the gasket slides at a low speed (100 mm/minute) inside the outer cylinder is not more than 20N. The outer cylinder of the syringe can be made of plastics.

The detailed description above describes various aspects of a gasket and a syringe embodying the gasket. However it is to be understood that the invention is not limited to the precise embodiment described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

The invention claimed is:

1. A gasket for use in a syringe so formed as to liquid-tightly and slidably contact an inner surface of an outer cylinder of said syringe,
    said gasket comprising a gasket body made of an elastic body and a coating layer formed on a portion thereof which contacts at least said syringe,
    wherein said coating layer comprises a composition containing a silicone resin which comprises a condensate of a reactive silicone having a terminal silanol group at both terminals thereof, and wherein the condensate contains a siloxane bond derived from said silanol group, wherein said coating layer does not contain solid fine particles,
    wherein said composition contains an alkylalkoxysilane or a phenylalkoxysilane as a second silicone compound different from said silicone resin having said siloxane bond, an aminoalkylalkoxysilane or a glycidoxyalkylalkoxysilane as a third silicone compound, and
    said gasket has a plunger which is mounted on said gasket body or is capable of being mounted thereon.

2. The gasket for use in the syringe according to claim 1, wherein said silicone resin is thermosetting.

3. The gasket for use in the syringe according to claim 1, wherein said coating layer has a thickness of 1 to 30 µm.

4. The gasket for use in the syringe according to claim 1, wherein an initial sliding resistance value of said coating layer is not more than a maximum value of a dynamic sliding resistance value thereof.

5. A syringe comprising an outer cylinder; and the gasket according to claim 1, which is slidably accommodated inside said outer cylinder.

6. The syringe according to claim 5, wherein the syringe contains a liquid medicine.

7. The syringe according to claim 5, wherein a dynamic sliding resistance value of said gasket when said gasket slides at a low speed of 100 mm/minute inside said outer cylinder is not more than 20 N.

8. The gasket for use in the syringe according to claim 1, wherein said reactive silicone having the terminal silanol group at both terminals thereof is both-terminal polydimethylsiloxane silanol.

9. The gasket for use in the syringe according to claim 1, wherein said alkylalkoxysilane is methyltrimethoxysilane.

10. The gasket for use in the syringe according to claim 1, wherein said aminoalkylalkoxysilane is 3-aminopropyltriethoxysilane.

11. The gasket for use in the syringe according to claim 1, wherein said glycidoxyalkylalkoxysilane is 3-glycidoxypropyltrimethoxysilane.

12. The gasket for use in the syringe according to claim 1, wherein said reactive silicone having the terminal silanol group at both terminals thereof is both-terminal polydimethylsiloxane silanol, said aminoalkylalkoxysilane is 3-aminopropyltriethoxysilane and said glycidoxyalkylalkoxysilane is 3-glycidoxypropyltrimethoxysilane.

13. The gasket for use in the syringe according to claim 1, wherein said coating layer is formed from a coating solution containing components composing the reactive silicone having the terminal silanol group at both terminals thereof, the alkylalkoxysilane and the aminoalkylalkoxysilane or the glycidoxyalkylalkoxysilane dispersed and suspended in purified water, and the coating layer is obtained by applying the coating solution to a surface of the gasket and thereafter curing the coating solution.

14. The gasket for use in the syringe according to claim 1, wherein said composition contains said aminoalkylalkoxysilane as said third silicone compound and said glycidoxyalkylalkoxysilane as a fourth silicone compound.

\* \* \* \* \*